US007220829B2

(12) United States Patent
Rossjohn et al.

(10) Patent No.: US 7,220,829 B2
(45) Date of Patent: May 22, 2007

(54) CYTOKINE BINDING DOMAIN OF CYTOKINE RECEPTORS

(75) Inventors: Jamie Rossjohn, Carnegie (AU); William John McKinstry, North Carlton (AU); Joanna May Woodcock, Crafers (AU); Michael William Parker, Newport (AU); Angel Francisco Lopez, Medindie (AU); Christopher James Bagley, Fullarton (AU)

(73) Assignee: Medvet Science Pty. Ltd., Adelaide (AU)

( * ) Notice: Subject to any disclaimer, the term of this patent is extended or adjusted under 35 U.S.C. 154(b) by 389 days.

(21) Appl. No.: 09/913,419

(22) Filed: Aug. 8, 2001

(65) Prior Publication Data

US 2003/0044975 A1 Mar. 6, 2003

Related U.S. Application Data

(63) Continuation of application No. PCT/AU00/00079, filed on Feb. 8, 2000.

(30) Foreign Application Priority Data

| Feb. 8, 1999 | (AU) | .................................. PP 8576 |
| Feb. 9, 1999 | (AU) | .................................. PP 8577 |
| May 11, 1999 | (AU) | .................................. PQ 0264 |

(51) Int. Cl.
C07K 14/715 (2006.01)

(52) U.S. Cl. ..................................... 530/350; 530/300
(58) Field of Classification Search ................. 530/350
See application file for complete search history.

(56) References Cited

FOREIGN PATENT DOCUMENTS

| WO | WO-97/07215 A | 2/1997 |
| WO | 97/28190 | 8/1997 |
| WO | 00/09561 | 2/2000 |

OTHER PUBLICATIONS

Callard and Gearing (1994) The Cytokine Factsbook, Academic Press Ltd. pp. 49-51.*
Mikayama et al. Proc. Natl. Acad. □i. USA vol. 90, pp. 10056-10060.*
Voet et al. Biochemistry John Wiley & Sons, Inc., pp. 126-128 and 228-234.*
Sun, Q. et al., A Monoclonal Antibody (MOAB) to the Human IL-3, GM-CSF and IL-5 Receptor Common Beta-Chain (BETAC) Neutralises the Binding and Function of All Three Ligands:m Blood, W.B. Saunders, Philadelphia, VA, US, vol. 88, No. 10 SUP01PT01/2, Nov. 15, 1996, p. 545A, Abstract.
Sun, Q., et al., "Simultaneous antagonism of interleukin-5, granulocyte-macrophage colony-stimulating factor, and interleukin-3 stimulation of human eosinophils by targetting the common cytokine binding site of their receptors", Blld, W.B. Saunders Company, vol. 94, No. 6, Sep. 15, 1999, Abstract, p. 1944.
Woodcock, J.M. et al., The human granulocyte-macrophage colony-stimulating factor (GM-CSF) receptor exists as a preformed receptor complex that can be activated by GM-CSF, Interleukin-3, or interleukin-5:, Blood, W.B. Saunders, vol. 90, No. 8, Oct. 15, 1997, p. 3006, Abstract.
Bagley, C.J., et al., The Structural and Functional Basis of Cytokine Receptor Activation Blood. Mar. 1997, vol. 89, No. 5, pp. 1471-1482.
Woodcock, J.M., et al., "A Single Tyrosine Residue in the Membrane-proximal Domain of the Granulocyte-Macrophage Colony=stimulating Factor . . . " The Journal of Biological Chemistry. Oct. 1996, vol. 271, No. 42, pp. 25999-26006.

* cited by examiner

*Primary Examiner*—Prema Mertz
(74) *Attorney, Agent, or Firm*—Darby & Darby

(57) ABSTRACT

The present invention provides a cytokine-binding domain or portion thereof which binds to at least one cytokine and is capable of transducing a cytokine signal through a single cytokine receptor, said domain comprising a portion of the B'-C' loop of domain 4 of a $\beta_c$ chain or analogous structure of a cytokine receptor. In another aspect of the invention there is provided a method of identifying a compound having cytokine agonist or antagonist activity, said method including subjecting a potential cytokine agonist and/or cytokine antagonist compound to a cytokine binding domain or portion thereof wherein said domain binds to at least one cytokine and is capable of transducing a cytokine signal through a single cytokine receptor, said domain comprising a portion of the B'-C' loop of domain 4 of a $\beta_c$ chain or analogous structure of the cytokine receptor; and determining the presence of an agonist or antagonist response of the compound on the activity of a cytokine. In a preferred aspect there is provided a method fo identifying a GM-CSF, IL-3 and IL-5 agonist or antagonist, said method including: subjecting a potential agonist or antagonist to a GM-CSF, IL-3 and IL-5 binding domain or portion thereof wherein said domain binds to at least one of the cytokines and is capable of transducing a cytokine signal through a single cytokine receptor, said domain comprising a portion of the B'-C' loop of domain 4 of a $\beta_c$ chain or analogous structure of the cytokine receptor; and determining the presence of a agonist or antagonist response from the compound on the activity of GM-CSF, IL-3 and IL-5.

18 Claims, 9 Drawing Sheets

SEQUENCE LISTING

```
<160> NUMBER OF SEQ ID NOS: 3

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: where X is any residue

<400> SEQUENCE: 1

Trp Ser Xaa Trp Ser
1               5

<210> SEQ ID NO 2
<211> LENGTH: 4
<212> TYPE: PRT
<213> ORGANISM: Homo sapiens
<220> FEATURE:
<221> NAME/KEY: MISC_FEATURE
<222> LOCATION: (365)..(368)
<223> OTHER INFORMATION: segment of mutant cytokine binding domain

<400> SEQUENCE: 2

Ala Ala Ala Ala
1

<210> SEQ ID NO 3
<211> LENGTH: 5
<212> TYPE: PRT
<213> ORGANISM: Homo sapiens

<400> SEQUENCE: 3

Trp Ser Glu Trp Ser
1               5
```

CYTOKINE BINDING DOMAIN OF CYTOKINE RECEPTORS

This is a continuation of international application Serial No. PCT/AU00/00079, filed Feb. 8, 2000, the entire disclosure of which is hereby incorporated by reference.

The present invention relates to a cytokine binding domain, and to a cytokine-binding antagonist and/or a cytokine-binding agonist. The invention further relates to methods of identifying such compounds and uses of such compounds in therapy, prevention and diagnosis.

BACKGROUND OF THE INVENTION

Heterodimeric cytokine receptors comprise two (or three) subunits which subserve distinct and specialised functions. These include a major ligand-binding subunit (the α subunit) and a signalling subunit (the β or γ subunit). Importantly, the latter is able to recognise several cytokines complexed to the appropriate α chain and transduce their signals. This is exemplified by the common β chain ($\beta_c$) of the human granulocyte-macrophage colony-stimulating factor GM-CSF, interleukin-3 (IL-3) and IL-5 receptors, the common IL-2 receptor γ chain (shared by the IL-2, IL-4, IL-7, IL-9 and IL-15 receptors) and gp130 (shared by the IL-6, IL-11, LIF, ciliary neutrophic factor, oncostatin M and cardiotrophin receptors). Significantly, IL-5, IL-3 and GM-CSF, the only three cytokines known to stimulate eosinophil production, can be found concomitantly elevated in lungs affected by allergic inflammation.

The simultaneous antagonism of all three GM-CSF, IL-3 and IL-5 may be desirable or indeed necessary for stimulating eosinophils. For example, eosinophils which are believed to be the major cell type involved in allergy can be maintained in numbers and be stimulated by either IL-3, GM-CSF or IL-5 (Lopez et al, 1989). Antagonism of all three cytokines may thus be necessary to inhibit the actions of eosinophils and basophils. Similarly, basophils which are also believed to play an effector role in allergy can be stimulated by either IL-3, GM-CSF or IL-5 (Lopez et al, 1990). Antagonism of GM-CSF, IL-3 and IL-5 may be accomplished by the concomitant administration of specific antagonists for each different cytokine. Though feasible, this approach has the disadvantage of having to administer up to three different proteins which is not only inconvenient but which also increases the risk of immunogenicity and other side-effects.

Because all three of these cytokines act through a common receptor subunit ($\beta_c$) it may be possible to simultaneously inhibit the action of GM-CSF, IL-3 and IL-5 with a single compound via the ($\beta_c$) subunit.

Thus, an antagonist directed against the $\beta_c$ chain may simultaneously inhibit the function of all three cytokines and may prove a useful therapeutic.

One of the major problems in seeking structural data of the binding site of a communal subunit complexed to cytokines is that, unlike homodimeric receptors or isolated α chains of heterodimeric receptors which can directly bind to cytokines, communal subunits cannot bind to cytokines by themselves. To overcome this problem applicants have developed a monoclonal antibody (Mab) against a region which is important for cytokine high affinity binding within domain 4 of the GM-CSF/IL-3/IL-5 common beta chain (D4$\beta_c$) receptor. This Mab, termed BION-1, inhibited the high affinity binding of GM-CSF, IL-3 and IL-5 to human eosinophils, and inhibited their in vitro production and functional activation. BION-1 thus represents the first common antagonist of the GM-CSF, IL-3 and IL-5 receptors and a unique tool with which to explore the cytokine-binding site in the common beta chain.

The molecular basis for the affinity conversion of $\beta_c$ to each ligand is not fully understood as the ligand-receptor complex had not yet been crystallised and this has prevented the structural definition of their ligand-binding sites. Applicants have now crystallised and determined the structure of the D4$\beta_c$ domain of the GM-CSF/IL-3/IL-5 receptor bound to an antagonist in the form of BION-1.

SUMMARY OF THE INVENTION

The present invention provides a cytokine-binding domain or portion thereof which binds to at least one cytokine and is capable of transducing a cytokine signal through a single cytokine receptor, said domain comprising a portion of the B'-C' loop of domain 4 of a $\beta_c$ chain (D4$\beta_c$) or analogous structure of a cytokine receptor.

More preferably, the domain comprises a portion of the B'-C' loop of domain 4 and a groove which is defined by the B'-C', F'-G' loops and the N-terminal section of domain 4 or an analogous structure.

In another embodiment, the domain further includes a Tyrosine residue capable of interaction with an α chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

Preferably the binding domain is capable of recognising at least two cytokines that have complexed to an α chain. Preferably these cytokines are selected from the group including, but are not limited to, IL-3, IL-5 and GM-CSF or from IL-4 and IL-13. The cytokines particularly IL-3, IL-5 and GM-CSF may bind via the common $\beta_c$ chain of the cytokine receptor having firstly been bound by the α chain and forming a cytokine: α chain complex.

In another aspect of the invention there is provided a method of identifying a compound having cytokine agonist or antagonist activity said method including:

subjecting a potential cytokine agonist and/or cytokine antagonist compound to a cytokine binding domain or portion thereof wherein said domain binds to at least one cytokine and is capable of transducing a cytokine signal through a single cytokine receptor, said domain comprising a portion of the B'-C' loop of domain 4 of a $\beta_c$ chain or analogous structure of the cytokine receptor; and determining the presence of an agonist or antagonist response from the compound on the activity of a cytokine.

More preferably, the domain comprises a portion of the B'-C' loop of domain 4 and a groove which is defined by the B'-C', F'-G' loops and the N-terminal section of domain 4 or an analogous structure.

The cytokine binding domain may be a domain of a receptor common to a number of cytokines. Preferably the domain is common to GM-CSF, IL-3 and IL-5 or is a common signalling structure common to IL-4 and IL-13.

In a preferred aspect there is provided a method of identifying a GM-CSF, IL-3 and IL-5 agonist or antagonist said method including:

subjecting a potential agonist or antagonist to a GM-CSF, IL-3 and IL-5 binding domain or portion thereof wherein said domain binds to at least one of the cytokines and is capable of transducing a cytokine signal through a single cytokine receptor, said domain comprising a portion of the B'-C' loop of domain 4 of a $\beta_c$ chain or analogous structure of the cytokine receptor; and determining the presence of an agonist or antagonist response from the compound on the activity of GM-CSF, IL-3 and IL-5.

More preferably, the domain comprises a portion of the B'-C' loop of domain 4 and a groove which is defined by the B'-C', F'-G' loops and the N-terminal section of domain 4 or an analogous structure.

In another preferred aspect of the invention there is provided a method of identifying a compound having a cytokine antagonist activity, said method including:

subjecting a potential cytokine antagonist to a cytokine binding domain or portion thereof wherein said domain or portion thereof binds to at least one cytokine and is capable of transducing a cytokine signal through a single cytokine receptor, said domain comprising a portion of the B'-C' loop of domain 4 of a $\beta_c$ chain or analogous structure of the cytokine receptor; and identifying a compound that has bound to the cytokine-binding domain wherein said compound has an antagonist response on the activity of the cytokine.

More preferably, the domain comprises a portion of the B'-C'loop of domain 4 and groove which is defined by the B'-C', F'-G' loops and the N-terminal section of domain 4 or an analogous structure.

In a preferred embodiment, there is provided a method for identifying an antagonist of GM-CSF, IL-3 and IL-5, said method including:

subjecting a potential cytokine antagonist to a cytokine binding domain or portion thereof wherein said domain or portion thereof binds to at least one of the cytokines and is capable of transducing a cytokine signal through a single cytokine receptor, said domain comprising a portion of the B'-C' loop of domain 4 of a $\beta_c$ chain or analogous structure of the cytokine receptor; and identifying a compound that has bound to the cytokine-binding domain wherein said compound has an antagonist response on the activity of the cytokine.

More preferably, the domain comprises a portion of the B'-C' loop of domain 4 and a groove which is defined by the B'-C', F'-G' loops and the N-terminal section of domain 4 or an analogous structure.

In another aspect of the invention there is provided a method of preventing or treating a cytokine—related condition, said method including administering to a subject an effective amount of a compound, agonist or antagonist identified by the methods as described above.

DETAILED DESCRIPTION OF THE INVENTION

Figure 1:
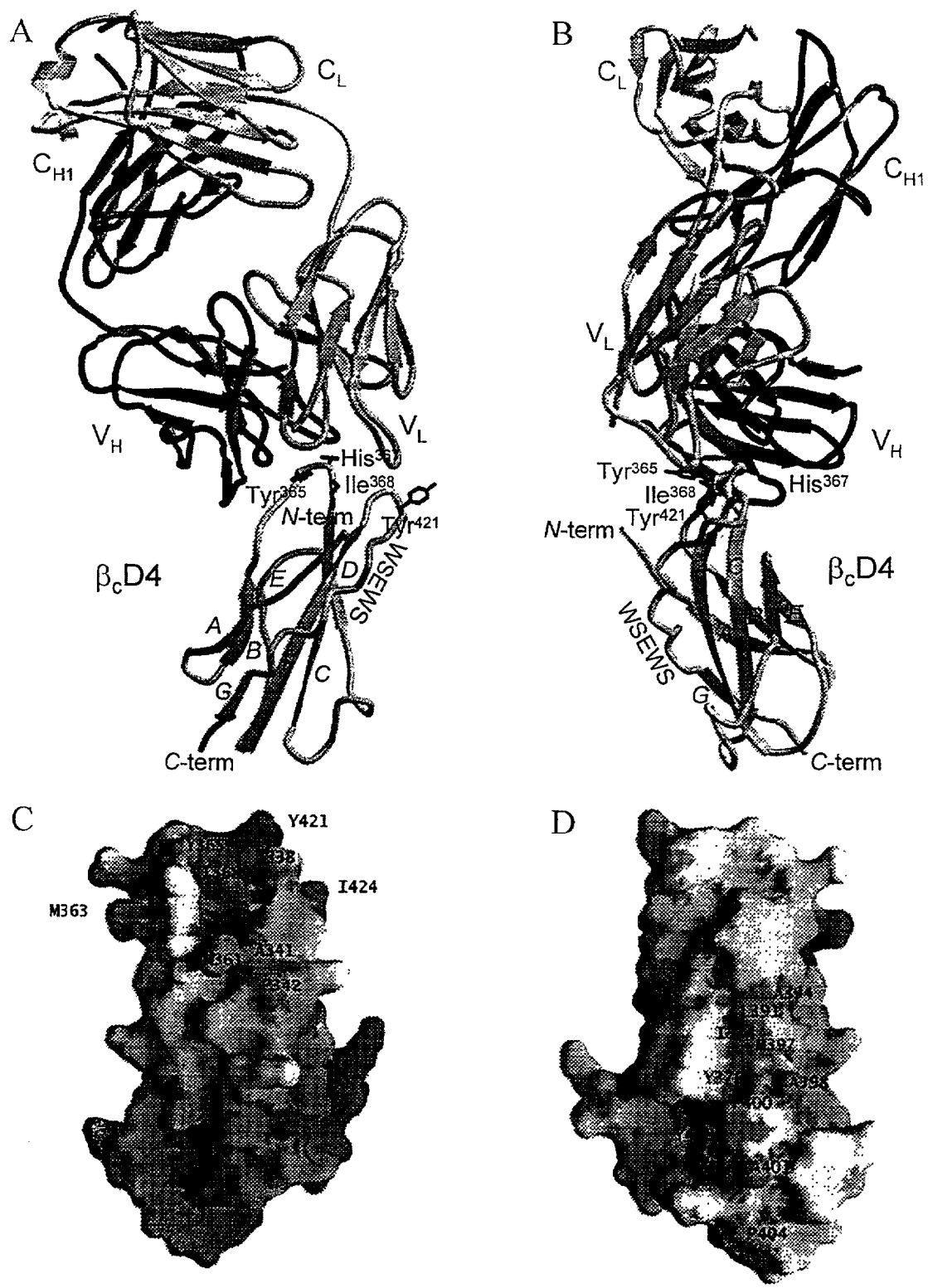
FIG. 1 illustrates the structure of $D4\beta_c$. (A) Structure of the Fab/receptor $\beta_c$ domain 4 ($D4\beta_c$) complex shown in ribbon representation. The MoAb heavy chain is shown in dark grey, the light chain and the receptor in light grey. The major structural features of $D4\beta_c$ are labelled and the locations of key residues are denoted by stick representation. These pictures were produced using Molscript (Kraulis, 1991) and Raster3D (Merrift and Murphy, 1994). (B) Structure as for (A) but reoriented 90° about the vertical axis. (C) Surface representation of the receptor using the program GRASP[35]. The dark surface indicates the location of hydrophobic/aromatic patch, $H_1$. The molecule is tilted approximately 20° counterclockwise relative to (A). (D) View of hydrophobic/aromatic patch, H2 prepared as for (C). The molecule is tilted approximately 20° clockwise and rotated approximately 60° clockwise from above about a vertical axis relative to (B).

The present invention provides a cytokine-binding domain or portion thereof which binds to at least one cytokine and is capable of transducing a cytokine signal through a single cytokine receptor, said domain comprising a portion of the B'-C' loop of domain 4 of a $\beta_c$ chain or analogous structure of a cytokine receptor.

More preferably, the domain comprises a portion of the B'-C' loop of domain 4 and a groove which is defined by the B'-C', F'-G' loops and the N-terminal section of domain 4 or an analogous structure of a cytokine receptor.

In another embodiment, the domain further includes a Tyrosine residue capable of interaction with an α chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

The term "chain" and "chain subunit" may be used interchangeably throughout the specification. For instance, the "α chain" is the same as the "α chain subunit."

Throughout the description and claims of the specification the word "comprise" and variations of the word, such as "comprising" and "comprises" is not intended to exclude other additives, components, integers or steps.

The term "equivalent residue" used herein means an amino acid residue which can perform a similar function.

Preferably the binding domain is capable of recognising and binding to at least two cytokines that have complexed to an appropriate α chain. Preferably these cytokines are selected from the group including, but are not limited to, IL-3, IL-5 and GM-CSF or to IL-4 and IL-13 The three cytokines IL-3, IL-5 and GM-CSF may be bound via the common $\beta_c$ chain of the cytokine receptor having firstly been bound by the α chain and forming a cytokine: α chain complex. Similarly, IL-4 and IL-13 may share a common signalling unit similar to the $\beta_c$ on the cytokine receptor.

The common $\beta_c$ chain may derive from any one of the following, including GM-CSF, IL-3 and IL-5 receptors. Common signalling subunits having similar structures to $\beta_c$ may be derived from the common IL-2 receptor γ chain (shared by the IL-2, IL-4, IL-7, IL-9 and IL-15 receptors) and gp130 (shared by the IL-6, IL-11, LIF, ciliary neutrophic factor, oncostatin M and cardiotrophin receptors) or from any one of the cytokine superfamily receptors but not limited to the group comprising LIFR, gp130, IL-2Rβ, IL-4R/IL-13R, IL-2Rγ, IL-3Rα, EPOR, TPOR and OBR or be selected from a related (class 1) cytokine receptor structure selected from the group including but not limited to growth hormone receptor (GHR), prolactin receptor (PRLR), erythropoietin receptor (EPOR), G-CSF receptor (G-CSFR) and gp130. The pairwise sequence identities between $D4\beta_{\beta c}$ and these receptors, after structure-based alignment, range from 12% (G-CSF) to 27% (gp130). There are only seven residues (Pro 343, Trp 358, Leu 402, Tyr 408, Arg 413, Gly 423, Ser 426) that are strictly conserved across the receptors, all of which appear to play structural roles. A structural superposition indicates that $D4\beta_c$ is most closely related to PRLR (r.m.s. deviation of 1.4 Å on 86 Cα atoms, 20% sequence identity) followed by GHR (r.m.s. deviation of 1.5 Å on 81 Cα atoms, 23% sequence identity).

Preferably, the common $\beta_c$ chain is derived from IL-5, IL-3 or GM-CSF receptor. These cytokines IL-3, IL-5 and GM-CSM are known to stimulate eosinophil production and can be found concomitantly elevated in lungs affected by allergic inflammation. Their simultaneous elevation may increase eosinophil numbers, contribute to the overall degree of eosinophil activation, be responsible for the different phases of eosinophil infiltration and determine a localised versus a generalised eosinophil-mediated inflammation. This may be particularly important in the pathology of certain disease such as asthma where the eosinophil plays an effector role.

The present invention describes the binding domain of the $\beta_c$. However this is illustrative only and is not to be considered a limitation on the invention described.

Applicants expressed the fourth (activation) domain of $\beta_c$ ($D4\beta_c$) in *E. coli* and purified it to homogeneity by ion exchange and reverse-phase high performance liquid chromatography. BION-1 MoAb was digested with papain to generate Fab fragments which were purified by chromatography on protein A sepharose. Titration of $D^{4\beta}_c$ and the BION-1 Fab produced a stoichiometric 1:1 complex that subsequently formed crystals. These crystals diffracted well enough to allow a full crystallographic structure determination to proceed.

The common $\beta_c$ chain of domain 4 ($D4\beta_c$) has been found by the Applicants to have a compact globular shape with overall dimensions of 45 Å×25 Å×20 Å (FIG. 1A). The N- and C-termini represent the sites of attachment for the remainder of the extracellular region and the membrane-spanning domain, respectively. The molecule adopts the topology of a fibronectin type III module with two anti-parallel beta-sheets (42% sheet) packing against each other via a multitude of hydrophobic interactions, including two clusters of aromatic residues (Trp 434, Tyr 354 and Tyr 376; Trp 358, Phe 372 and His 370). Sheet A consists of three beta-strands (A'(residues 344 to 350), B'(residues 353 to 359) and E'(residues 396 to 398)) and sheet B consists of four strands (C'(residues 369 to 378), D'(residues 389 to 392), F' and F"(residues 406 to 417) and G'(residues 432 to 436)) with the longest strand, C', almost spanning the length of the molecule. The amino acid sequence motif, WSXWS (where X is any residue), a characteristic feature of many cytokine receptors, is located between the F strand, preferably the F''' and the G strand, preferably the G' strands and adopts a double β-bulge structure (FIG. 1A). Arginine residues from strand F' interdigitate between the tryptophan residues of the motif to form a ladder of alternating basic and aromatic residues. The ladder is extended in each direction by additional aromatic and basic residues: Tyr 421-Arg 415-Trp 425-Arg 413-Trp 428-Arg 411-Trp 383-Arg 377-Trp 409-Arg 407. There is a "side-step" in the ladder at Arg 377-Trp 409. This ten-rung ladder, measuring 29 to 35 Å long, preferably 29 Å long with rungs of about 5 Å wide, represents the only significant electropositive patch on the surface of the molecule.

The crystallographic analysis is provided below in Table 1.

TABLE 1

| Crystallographic analysis | | | |
|---|---|---|---|
| Data collection | | | |
| Temperature of collection (K) | 100 | Multiplicity | 2.8 |
| | | I/σ$_I$ | 11.4 |
| Resolution limit (Å) | 2.8 | No. of data > 2σ$_I$ (%) | 66.2 |
| Observations | 58,732 | R$_{merge}$$^a$ (%) | 9.8 |
| Unique reflections | 21,211 | | |
| Completeness (%) | 88.1 | | |
| Refinement statistics | | | |
| Resolution range (Å) | ∞–2.8 | r.m.s. deviations from ideality | |
| R$_{factor}$$^b$ (%) | 22.8 | bond lengths (Å) | 0.010 |
| R$_{free}$$^b$ (%) | 28.8 | bond angles (°) | 1.55 |
| | | impropers (°) | 0.95 |
| | | dihedrals (°) | 27.1 |
| Atoms in model | | | |
| protein (non-hydrogen) | 4,146 | | |
| water | 124 | | |
| carbohydrate | 14 | | |
| Residues in most favored $^c$regions of Ramachandran plot (%) | | | 80 |
| Residues in additionally allowed $^c$regions of Ramachandran plot (%) | | | 19 |

$^a$R$_{merge}$ = Σ$_{hkl}$Σ$_I$|I$_j$ − <I>|/I</>|, where I$_j$ is the intensity for the ith measurement of an equivalent reflection with indices h, k, l.
$^b$R$_{factor}$ = 100(Σ|F$_o$| − |F$_c$||/Σ|F$_o$|) using all data except 6% which were used for the R$_{free}$ calculation.
$^c$Defined in Laskowski, R. A. et al (1993).

Besides the ladder, there are three other significant surface features worth noting. There are two large hydrophobic patches on the surface. The first, H1, is a dense strip of hydrophobic residues located at one edge of the β-sandwich defined by the D' and E' strands and measures 27 Å long and 6 Å in width (FIG. 1D). The second, H2, located on the opposite face to the first, forms part of a lip at the end of a pronounced groove on the surface of the molecule (FIG. 1C). The H2 patch is made up of residues Ile 338, Ala 341, Met 361, Tyr 365, and preferably including Met 340 and Pro 342 and the aliphatic moiety of Lys 362 and preferably including Ile 368 and Tyr 421. The groove is located at the N-terminal end of the molecule where one wall is formed by the B'-C' loop and part of the F''-G' loop and the other wall by the N-terminus (residues 338 to 342) (FIG. 1C).

The B'-C' loop of domain 4 or the common $\beta_c$ chain (D4$\beta_c$) of the cytokine receptor or part thereof is involved in the cytokine binding. The B-C and preferably the F-G loops protrude significantly from the body of the protein and are implicated in cytokine binding (FIGS. 1A,B). It adopts a regular structure in D4$\beta_c$ having residues 365 to 368 forming a type I $\beta$-turn (FIG. 1). Preferably the portion of a the B'-C' loop of the domain includes Tyr 365, Ile 368 and His 367. GCSFR, GHR, and PRLR have an aromatic residue equivalent to Tyr 365, whereas there is no corresponding residue to His 367.

In the interaction of a cytokine with the B'-C' loop it is further preferable that the residues Tyr 365, His 367 and Ile 368 are involved in the interaction of the cytokine and the receptor. Ideally, the Tyr 365, His 367 and Ile 368 form a cytokine binding triad that converges to form a pivot point to which all three cytokines (GM-CSF, IL-3 and IL-5) may bind via essential glutamate residues (Glu 21 of GM-CSF, Glu 22 of IL-3 and Glu13 of IL-5).

The F'-G' loop adopts a type IV $\beta$ turn at its tip in D4$\beta_c$ and the most significant features in this region are Arg 418 and Tyr 421, each of which projects out of solution (FIG. 1A). Accordingly, when the cytokine interacts with the $\beta_c$ chain, the Tyr 421 may interact with Domain 3 of $\beta_c$ and/or the $\alpha$-chain to enhance receptor-receptor interaction or oligermerisation.

More preferably, the domain comprises a portion of the B'-C' loop of domain 4 and a groove which is defined by the B'-C', F'-G' loops and the N-terminal section of domain 4.

In another embodiment, the domain further includes a Tyrosine residue capable of interaction with an $\alpha$ chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

In a further preferred embodiment the binding domain or portion thereof capable of binding the cytokine may be defined by an area bordered by any of the following residues Lys 362, Tyr 365, His 367, Ile 368, Arg 418, Gly 420, Asn 422, Thr 416, Ile 338, Gln 339, Met 340 and Met 361 or similar residues of common signalling units in other receptors. A majority of these residues are in the B'-C' loop and hence constitute a portion of the B'-C' loop capable of transducing a cytokine signal. The binding domain may be described as a "groove" comprising a concave surface formed largely, but not exclusively by hydrophobic residues, preferably of those listed above.

The hydrophobic surface patches, H1 and H2, of D4$\beta_c$ (FIGS. 1C, 1D) have corresponding features in most of the other receptors. With the exception of gp130, all the receptors possess significant hydrophobic patches equivalent to the location of H1 (centred about the D'-E' strand connection), although the degree and extent of hydrophobicity varies greatly. The equivalent region to H2 is conserved in all but gp130. By analogy with the other receptors, the H2 patch of D4$\beta_c$ might interact with the A-B loop from domain 3 of the intact receptor.

The interactions between D4$\beta_c$ and an antagonist such as BION-1 or a cytokine are summarized in Table 2 below.

TABLE 2

Interactions between D4$\beta_c$ and BION-1 or cytokines

| Residue identity | residue type | vdw contact[1] | buried area (Å$^2$)[2] | Polar interactions[3] | Required for binding BION-1[4] | Required for affinity-conversion[5] |
|---|---|---|---|---|---|---|
| D4$\beta_c$ | | | | | | |
| $\beta_c$ 361 | Met | No | 0 | | No | No |
| $\beta_c$ 362 | Lys | Yes | 45 | N$\zeta$ → L94:O$\delta$ | No | No |
| $\beta_c$ 363 | Met | Yes | 121 | S$\delta$ → H57:N | ? | No |
| $\beta_c$ 364 | Arg | Yes | 33 | N$\eta$ → H33:O$\eta$ <br> O → H33:O$\eta$ | ? | No |
| $\beta_c$ 365 | Tyr | Yes | 87 | O$\eta$ → L94:O$\delta$ | No | Yes |
| $\beta_c$ 366 | Glu | Yes | 165 | O$\epsilon$ → H35:N$\zeta$ <br> O$\epsilon$ → H33:N | Yes | No |
| $\beta_c$ 367 | His | Yes | 99 | N$\epsilon$ → L91:O | No | Yes |
| $\beta_c$ 368 | Ile | No | 16 | | No | Yes |
| $\beta_c$ 369 | Asp | No | 0 | | No | No |
| $\beta_c$ 370 | His | No | 0 | | No | No |
| $\beta_c$ 395 | His | No | 26 | | N.D.[6] | N.D. |
| $\beta_c$ 416 | Thr | Yes | 29 | O$\gamma$ → L28:O$\eta$ | N.D. | N.D. |
| $\beta_c$ 418 | Arg | Yes | 101 | N$\eta$ → H97:O | Yes | No |
| $\beta_c$ 419 | Thr | No | 15 | | No | No |
| $\beta_c$ 420 | Gly | No | 0 | | No | No |
| $\beta_c$ 421 | Tyr | Yes | 45 | | No | Yes |
| $\beta_c$ 422 | Asn | No | 0 | | No | No |
| BION-1 light chain | | | | | | |
| L 28 | Tyr | Yes | 162 | O$\eta$ → $\beta_c$416:O$\gamma$ | | |
| L 29 | Gly | No | 21 | | | |
| L 30 | Asp | No | 18 | | | |
| L 32 | Phe | Yes | 39 | | | |
| L 91 | Asn | Yes | 17 | O → $\beta_c$367:N$\epsilon$ | | |
| L 92 | Asn | No | 14 | | | |
| L 93 | Glu | No | 13 | | | |
| L 94 | Asp | Yes | 48 | O$\delta$ → $\beta_c$362:N$\zeta$ <br> O$\delta$ → $\beta_c$365:O$\eta$ | | |
| L 96 | Trp | Yes | 31 | | | |

TABLE 2-continued

Interactions between D4β$_c$ and BION-1 or cytokines

| Residue identity | residue type | vdw contact[1] | buried area (Å$^2$)[2] | Polar interactions[3] | Required for binding BION-1[4] | Required for affinity-conversion[5] |
|---|---|---|---|---|---|---|
| BION-1 heavy chain | | | | | | |
| H 32 | Tyr | Yes | 6 | | | |
| H 33 | Tyr | Yes | 100 | Oη → β$_c$364:Oη<br>Oη → β$_c$364:O<br>N → β$_c$366:Oε | | |
| H 35 | Lys | No | 0 | Nζ → β$_c$366:Oε | | |
| H 51A | Asn | Yes | 21 | | | |
| H 53 | Asn | No | 37 | | | |
| H 55 | Gly | Yes | 9 | | | |
| H 57 | Thr | Yes | 18 | Oγ → β$_c$363:Sδ | | |
| H 58 | Leu | No | 52 | | | |
| H 96 | Asp | Yes | 6 | | | |
| H 96A | Gly | Yes | 51 | | | |
| H 97 | Ile | Yes | 13 | O → β$_c$418:Nη | | |
| H 100A | Gly | Yes | 16 | | | |

[1] vdw contacts of c with BION-1 or vice versa
[2] area of solvent-exposure lost on formation of the D4β$_c$/BION-1 complex, calculated using dssp Kabsch, W.S. et al (1983) Biopolymers 22, 2577
[3] Includes salt bridges and hydrogen bonds, based on the distance and geometric criteria of Kabsch & Sander Kabsch, W. S. et al (1983) Biopolymers 22, 2577
[4]Based on mutation to alanine from Sun, Q et al (1999) Blood, 1943
[5]Based on mutation to alanine from Woodcok, J. M et al (1994) EMBO. J. 13, 5176, Woodcok, J M et al, J. Biol. chem., 271, 25999.
[6]N.D. not determined In another aspect of the invention there is provided a method of identifying a compound having cytokine agonist or antagonist activity said method including subjecting a potential cytokine agonist and/or cytokine antagonist compound to a cytokine binding domain or portion thereof wherein said domain binds to at least one cytokine and is capable of transducing a cytokine signal through a single cytokine receptor, said domain comprising a portion of the B'-C' loop of domain 4 of a $\beta_c$ chain or analogous structure of the cytokine receptor; and determining the presence of an agonist or antagonist response of the compound on the activity of a cytokine.

More preferably, the domain comprises a portion of the B'-C' loop of domain 4 and a groove which is defined by the B'-C', F'-G' loops and the N-terminal section of domain 4 or an analogous structure.

In another embodiment, the domain further includes a Tyrosine residue capable of interaction with an α chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

The common $\beta_c$ chain may be common to IL-3, IL-5 or GM-CSF or it may be similar structure common to IL-4 and IL-13.

The agonist or antagonist response may be measured by the ability of the compound to bind and activate or inhibit a cytokine response or it may be measured by an inability to bind to a mutant cytokine binding domain. This can be measured by cellular activities associated with any of the cytokines. For instance, with the cytokines IL-5, GM-CSF and IL-3 stimulation of eosinophil adherence, priming for degranulation and cytotoxicity, and propagation of viability may be measured in the presence or absence of the agonists or antagonists binding to the cytokine binding domain or a portion thereof as hereinbefore described.

In a preferred aspect there is provided a method of identifying a GM-CSF, IL-3 and IL-5 agonist or antagonist said method including:

subjecting a potential agonist or antagonist to a GM-CSF, IL-3 and IL-5 binding domain or portion thereof wherein said domain binds to at least one of the cytokines and is capable of transducing a cytokine signal through a single cytokine receptor, said domain comprising a portion of the B'-C' loop of domain 4 of a $\beta_c$ chain or analogous structure of the cytokine receptor; and determining the presence of an agonist or antagonist response from the compound on the activity of GM-CSF, IL-3 and IL-5.

More preferably, the domain comprises a portion of the B'-C' loop of domain 4 and a groove which is defined by the B'-C', F'-G' loops and the N-terminal section of domain 4 or an analogous structure.

In another preferred aspect of the invention there is provided a method of identifying a compound having a cytokine antagonist activity, said method including:

subjecting a potential cytokine antagonist to a cytokine binding domain or portion thereof wherein said domain or portion thereof binds to at least one cytokine and is capable of transducing a cytokine signal through a single cytokine receptor, said domain comprising a portion of the B'-C' loop of domain 4 of a $\beta_c$ chain or analogous structure of the cytokine receptor; and identifying a compound that has bound to the cytokine-binding domain wherein said compound has an antagonist response on the activity of the cytokine.

More preferably, the domain comprises a portion of the B'-C' loop of domain 4 and a groove which is defined by the B'-C', F'-G' loops and the N-terminal section of domain 4 or an analogous structure.

In another embodiment, the domain further includes a Tyrosine residue capable of interaction with an α chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

In a preferred embodiment, there is provided a method for identifying an antagonist of GM-CSF, IL-3 and IL-5, said method including:

subjecting a potential cytokine antagonist to a cytokine binding domain or portion thereof wherein said domain or portion thereof binds to at least one of the cytokines and is capable of transducing a cytokine signal through a single cytokine receptor, said domain comprising a portion of the B'-C' loop of domain 4 of a $\beta_c$ chain or analogous structure of the cytokine receptor; and identifying a compound that has bound to the cytokine-binding domain wherein said compound has an antagonist response on the activity of the cytokine.

More preferably, the domain comprises a portion of the B'-C' loop of domain 4 and a groove which is defined by the B'-C', F'-G' loops and the N-terminal section of domain 4 or analogous structure.

In another embodiment, the domain further includes a Tyrosine residue capable of interaction with an α chain subunit or with Domain 3 of the $\beta_c$ chain subunit to allow high affinity binding of the cytokine. In a further preferred embodiment, the tyrosine is Tyr 421 or equivalent residue. The Tyr 421 or equivalent residue improves $\beta_c$ intramolecular interactions and/or the receptor subunit-receptor subunit interaction or oligomerisation.

The antagonist preferably inhibits the binding of cytokines preferably IL-3, IL-5 and GM-CSF to the $\beta_c$ or IL-4 and IL-13 to a common signalling unit similar to $\beta_c$ via a portion of the B'-C' loop or similar structure. Preferably that portion is identified by the "groove" or part thereof as described above. The cytokines may bind the common $\beta_c$ chain or common signalling unit and more particularly to a portion of the B'-C' loop.

In a further preferred embodiment, the antagonist may attach, target or block Tyr 421 or equivalent residue, as well as the amino acids or groups of amino acids that interact with Tyr 421 or equivalent residue in either the Domain 3 of the $\beta_c$ subunit or the α chain subunit.

The methods identified above will allow the identification and design of agonists and antagonist of cytokines that can act through the portion of the $\beta_c$ or other common signalling units and/or through the Tyr 421 or equivalent residue and/or Domain 3 of the $\beta_c$ chain subunit and/or the α chain subunit of a cytokine receptor or an analogous common chain in other receptors. Preferably the subunit is common to GM-CSF, IL-3 and IL-5 such as $\beta_c$ or is an analogous chain common in other receptors such as in IL-4 and IL-3.

A crystalline form of the cytokine binding domain is also provided in the present invention and will allow for structure based design of drugs or targeted selection by phage display. Potential agonists and antagonists may be identified by screening for "groove binders" (compounds that may bind in the groove). These may be determined by considering wild type versus mutant domain 4 molecules. Mutants may be generated using mutations to alanines in the floor of the groove. Mutations may be directed to any of the residues selected from the group including Gln 340, Ile 338 and Met 361 to make the mutants.

Further uses of the structure of domain 4 of the common $\beta_c$ allows for affinity maturation using designed mutations such as those in the floor of the groove and including mutations at Gln 340, Ile 338 and/or Met 361. Because applicants have deduced the structure of domain 4, antigen structures are further understood by the present description and development of BION-1 mimetics either peptide or non-peptide is included in the scope of this application.

In another aspect there is provided a compound, agonist or antagonist identified by the methods described above. The compound agonist or antagonist may be an antibody or fragment thereof directed to the cytokine binding domain or more preferably the $\beta_c$ chain subunit of the cytokine receptor domain or an analogous common chain in other receptors. Even more preferably, the antibody or fragment thereof may be directed to a portion of the B'-C' loop of Domain 4 of a $\beta_c$ chain subunit or analogous structure of a cytokine receptor or the antibody may be directed to the Tyr 421 or equivalent residue or amino acids or groups of amino acids that interact with Tyr 421 or equivalent residue in either the Domain 3 of the $\beta_c$ chain subunit or the α chain subunit. The antibody may be monoclonal or polyclonal or an active portion thereof.

Methods of making such antibodies will be familiar to those skilled in the art and will be understood to further include the steps of inoculating an animal with a peptide molecule having the cytokine binding domain or a portion thereof as described above, fusing antibody producing cells with a myeloma cell line and screening for a cell line that produces an antibody reactive with the cytokine-binding domain or portion thereof, and harvesting antibodies from the cell line, testing for inhibition of high affinity binding and testing for inhibition or excitation of function. This may further include making small fragments of antibodies produced by the said cell line capable of binding the cytokine binding domain or portion thereof. The cell line may conveniently be a mouse cell line and the method may include the further step of "humanising" the said antibody fragments by replacing mouse sequences with human sequences in the non-binding regions. Humanising may be conducted by any methods known to the skilled addressee.

The antibody fragment may be a larger portion such as Fab fragments or much smaller fragments of the variable region. These fragments may be used as separate molecules or alternatively may form part of a recombinant molecule which is then used for therapeutic purposes. Thus for example the monoclonal antibody may be "humanised" by recombining nucleic acid encoding the variable region of the monoclonal antibody with nucleic acid encoding non-variable regions of human origin in an appropriate expression vector.

The agonist and antagonist compounds of the present invention are not limited to antibodies reactive to the cytokine-binding domain or any portions thereof and which compete with the binding with cytokines. Other compounds including small molecules or synthetic or natural chemical compounds capable of competing with the binding of a cytokine to the cytokine-binding domain or any portion thereof are also included in the present invention.

In another aspect of the invention there is provided a method of preventing or treating a cytokine—related condition, said method including administering to a subject an effective amount of a compound, agonist or antagonist as described above.

The compound, agonist or antagonist may be used singularly or in combination with other therapeutic agents such as corticosteroids.

The cytokine related condition may be a condition associated with any one of the group including GM-CSF, IL-3 and IL-5 or IL-4 and IL-13 or a condition which requires the binding of the cytokines to a common $\beta_c$ chains or to an analogous common chain in other receptors.

The examples below recite the use of antibodies to the cytokine binding domain as antagonists. However other compounds capable of inhibiting the binding of cytokine will be equally applicable.

The antagonist effect preferably leads to blocking of at least one function of any one of the cytokines which may be bound to a common $\beta_c$ chain or an analogous common chain. One of the benefits that is proposed to be derived from these antagonists is their use in modifying cells stimulated by one of the cytokines, and more in one specific form modifying the activity of the cytokines is proposed to impact greatly on cellular functions including eosinophil function. Therefore preferably the activity leads to inhibition of stimulation of effector cell activation and where the antibody or fragment thereof is to be used for treatment of asthma (for example), it leads most preferably to inhibition of IL-5, IL-3 and GM-CSF or IL-4 and IL-13 mediated eosinophil activation. It will be understood however that cells other than eosinophils are also the effectors of adverse conditions in humans and animals as a result of stimulation by these cytokines and inhibition of such stimulation is also contemplated by this invention These include cells that express either one or all of GM-CSF, IL-3 and IL-5 receptors, or the IL-4 and IL-13 receptors the stimulation of which leads to pathology. Examples of these are leukaemic cells, endothelial cells, breast cancer cells, prostate cancer cells, small cell lung carcinoma cells, colon cancer cells, macrophages in chronic inflammation such as rheumatoid arthritis and dendritic cells for immunosuppression.

A number of different facets of eosinophil function might be modified so that in one form IL-5, IL-3 and GM-CSF or IL-4 and IL-13 mediated eosinophil survival is inhibited or blocked. In a further form IL-5, IL-3 and GM-CSF, or IL-4 and IL-13 mediated eosinophil activation is inhibited or blocked.

The treatment may be aimed at being preventative by reducing the risk of contracting the condition, or the treatment may be used to alleviate or obviate the condition. The administration of the therapeutic agent can be any pharmaceutically acceptable form and in a suitable carrier.

It is postulated by the applicants that the construction of compounds that bind a portion of the B'-C' loop of the $\beta_c$ chain subunit or the Tyr 421 or equivalent residue as well as the amino acid or groups of amino acids that interact with Tyr 421 or equivalent residue in either the Domain 3 of the $\beta_c$ chain subunit or the $\alpha$ chain subunit will be therapeutically useful for intervention in conditions where IL-3, GM-CSF and IL-5 or IL-4 and IL-13 play a pathogenic role, mainly allergy, asthma, leukaemia, lymphoma and inflammation including arthritis.

Similarly for other cytokine receptors it is thought that antagonists or agonists will be therapeutically useful.

Since gp130 is functionally analogous to $\beta_c$ in the GM-CSF/IL-3/IL-5 receptor system, in that it is a common binding subunit and signal transducer for the IL-6, oncostatin M (OSM), ciliary neurotrophic factor (CNTF), leukaemia inhibitory factor (LIF) and IL-11, it is suggested that targeting/blocking of this cytokine binding domain will lead to antagonism of the IL-6, LIF, OSM CNTF and IL-11. Antagonism of this receptor system will be useful in inflammation, leukaemia and lymphoma. Antagonist of IL-2R$\beta$/$\gamma$ may be useful as immunosuppressants. Antagonists of LIFR may be useful for the prevention of implantation of embryos in utero. Antagonist of IL-4/IL-13 will inhibit IgE production and may be useful in treating asthma and allergies. [M. Willis-Karp et al (1998)].

Antagonist of IL-3 may be useful in treating allergy and follicular B cell lymphoma. Antagonists of IL-4 may inhibit IgE production, and be useful for treatment of asthma and allergy. Antagonists of IL-6R may be useful as an anti-inflammatory and may be used to inhibit myeloma growth. Antagonists against IL-7 may be useful as an immunosuppressant. Antagonists of the leptin receptor (OBR) may be useful in the treatment of cachexia, weight loss in conditions such as AIDS, cancer and parasitic diseases.

Agonists agents that bind to $\beta_c$ via the B'-C' loop as described above may be used to stimulate hemopoesis, and to boost an immune response against microorganisms and parasites. Agonist agents that bind to LIFR may be useful in the suppression of embryonic stem cell differentiation. Agonists agents that bind to IL-2R$\beta$ may be used in immunostimulation. Agonists agents that bind to IL-4R/IL-13 may have anti-tumour activity.

Agonists agents that bind to specific subunits IL-3R may be used in the in vivo and ex vivo expansion of early hemopoietic cells. Agonists agents that bind to IL-4R may have useful anti-tumour activity. Agonists agents that bind to IL-7R may have useful anti-tumour immunity. Agonists agents that bind IL-11 may prove a useful adjunct to cancer therapy. Agonists agents that bind to EPOR may be used to correct anaemia of chronic renal failure, of chronic inflammatory diseases and of malignant diseases. Agonists agents that bind to TPOR, may be useful for correcting thrombocytopenia (such as may be associated with chronic inflammatory diseases, malignancies, chemo- and radio-therapy).

Examples of useful agonists are those for erythropoietin and thrombopoietin to elevate erythrocyte and platelet numbers in blood following blood cell loss, chemotherapy, radiotherapy, immunosuppression or bone marrow transplantation. Agonists of OBR may be used to induce weight loss, and in particular for obesity which is considered to be a contributing factor of hypertension, coronary heart disease and noninsulin-dependent diabetes mellitus. The molecules whether agonist or antagonist can be isolated on the basis of their ability to interact with the cytokine binding domain as described above.

The present invention will now be more fully described with reference to the following examples. It should be understood, however, that the description following is illustrative only and should not be taken in any way as a restriction on the generality of the invention described above.

EXAMPLES

Example 1

Crystallised BION-1-D4$\beta_c$ Complex

D4$\beta_c$ (residues 338-438 with an additional N-terminal Met) was expressed using the pEC611 vector in *E. coli* and purified by reverse-phase HPLC. The expressed protein was insoluble but could be recovered from the bacteria by dissolution in 6 M guanidine-HCl and 50 mM sodium acetate buffer pH 4.0. After HPLC the protein was dialysed exhaustively against 5 mM MES buffer pH 6.0. The BION-1 MoAb was raised against D$^{4\beta}_c$ (Sun, Q. et al (1999) Blood, 1943) and Fab fragments were generated and purified by standard methods. The complex was produced by mixing BION-1 Fab and D4β$_{βc}$ to give a 1:1 (mol/mol) complex which was purified on a Superdex 75 (Amersham Pharmacia) gel filtration column. Crystals of the complex were grown by the hanging-drop vapor diffusion method at 22° C. 2 μl droplets of protein solution (protein concentration of 5-7 mg ml$^{-1}$) were mixed with 1.5 μl of the reservoir solution and equilibrated against a 1 ml reservoir consisting of 100 mM citrate buffer pH 5.5 containing 12% (w/v) polyethylene glycol 4000. The crystals reached maximum size of approximately 0.6 mm×0.2 mm×0.2 mm over 10 days. The crystals belonged to space group P4$_1$2$_1$2 with cell dimensions a=b=77.6 Å, c=294.9 Å. The crystals were micro-manipulated, washed several times in reservoir buffer, dissolved in SDS-Tricine sample buffer and gel electrophoresis performed to confirm that the crystals were of the intact complex. The crystals proved to be sensitive to radiation and hence cryocooling was essential. However, the crystals were fragile and an array of commonly used cryoprotectants caused disordering of the crystals. A flash-freezing protocol was eventually established which involved soaking the crystals in 5% (v/v) increments of 2-methyl-2,4-pentanediol for two minutes till a final concentration of 15% (v/v) 2-methyl-2,4-pentanediol. A native data set was collected from a single flash-frozen crystal in-house on a MAR-Research imaging plate area detector with CuKa X-rays generated by a Rigaku RU-200 rotating anode generator. The cryoprotectant used was 15% MPD. The diffraction data were processed and analysed using DENZO and SCALEPACK [Z. Otwinowski and W. Minor, (1997)] and programs in the CCP4 suite (Daresbury Laboratory, UK). The processing resulted in a 91% complete data set to 3.3 Å resolution consisting of 13,143 unique reflections. The overall R$_{sym}$ was 12.4% and the multiplicity was 2.5. (See Crystallographic Analysis in Table 1).

The crystal structure was solved by molecular replacement using AMoRe (Navaza, J. (1994)) and the in-house native data set. Non-redundant Fab fragments were downloaded from the protein databank (PDB) and systematically tested as molecular replacement search probes. The second search probe tested, a mouse Fab fragment with PDB identifier 1YEC(Charbonnier, J. B. et al (1997)), proved successful. The tenth peak in the rotation function (peak height of 3.3 σ) produced the highest peak in the translation function (with a correlation coefficient of 27.9 and R$_{factor}$ of 54.1% compared with the next highest peak which had a correlation coefficient of 17.3 and R$_{factor}$ of 57.5%). The statistics indicated that P4$_1$2$_1$2 was the correct enantiomorphic space group. Rigid body refinement of the initial solution lead to a model with a correlation coefficient of 28.7 and a R$_{factor}$ of 49.9% (resolution range of 10.0 Å to 4.5 Å). Further refinement in which the Fab domains were treated as separate rigid bodies resulted in further improvement of the statistics (R$_{factor}$ of 46.1% and a drop of R$_{free}$ from 50.9% to 43.8%). Maps calculated from this solution yielded readily interpretable density for D4β$_c$. The model of the complex was then built with the help of skeletonized maps using the program O (Jones, T. A. (1991)) and refined using the maximum likelihood target in the program package CNS (Brunger, A. T. et al (1998)). The refinement was completed with the synchrotron native data set (Table 1). In the final stages a bulk solvent correction and restrained individual isotropic B-factors were applied. The quality of the final map was very good with no breaks in the main-chain connectivity and the real space fit (Jones, T. A. (1991)) of residues into the map never fell below 0.7. The final model comprises residues 338 to 438 for D4β$_c$, all residues for the Fab fragment, 124 solvent molecules and one carbohydrate unit, an N-acetylglucosamine unit, off the BION-1 residue Asn$^{26L}$. The choice of solvent molecules was conservative: they were only accepted if they appeared as peaks with a signal of more than 3 times the r.m.s. error in difference maps, reappeared in subsequent 2F$_o$-F$_c$ maps, took part in at least one hydrogen-bonding interaction and had temperature factors less than 80 Å$^2$. The stereochemical quality of the final model is good (Table 1) and other stereochemical parameters such as side-chain chi angle values, peptide bond planarity, alpha-carbon tetrahedral distortions and non-bonded interactions are all significantly better than the allowed ranges according to PROCHECK (Laskowski, R. A. et al (1993)). The correctness of the tracing is supported by residue omit maps (where 10% of the model was deleted, a round of simulated annealing performed to reduce bias and the resultant map examined in the region of omission) and 3D-1D scores that never fall below 0.2 indicating no residues are in chemically unreasonable environments (Luthy, R. et al (1992)).

Example 2

Model of Complex Between α Chain, Domains 3 and 4 of β$_c$ and GM-CSF, IL-5 and IL-3

In order to understand why the β$_c$ chain recognises all three cytokines, applicants have modelled the complex between α chain, domains' 3 and 4 of β$_c$ and each cytokine.

Figure 3A:
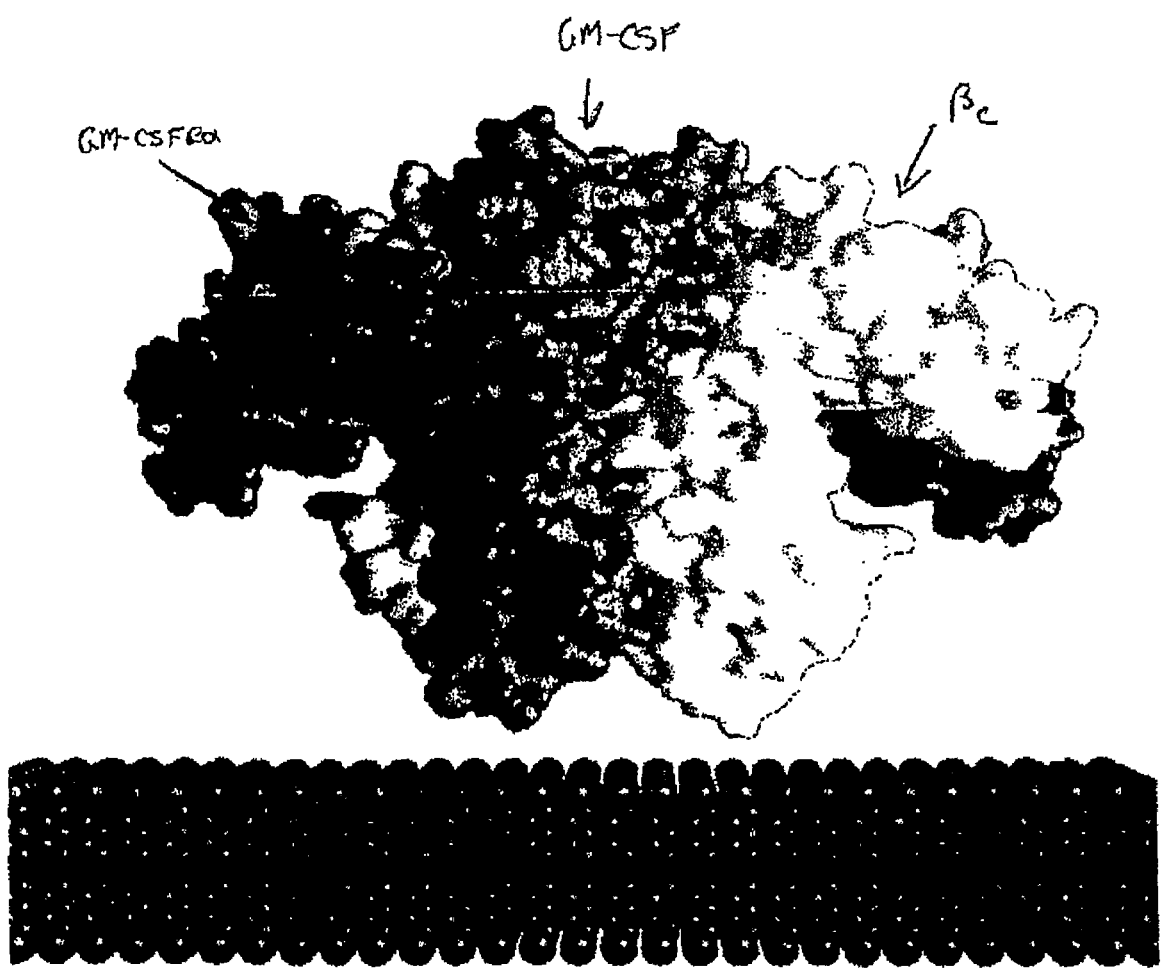
FIG. 3 illustrates a surface representation of the hexameric GM-CSF receptor complex model, looking side-on (A) and from above (B). α chain is in red, β chain in yellow, and each GM-CSF monomer in magenta and cyan.
Figure 3B:
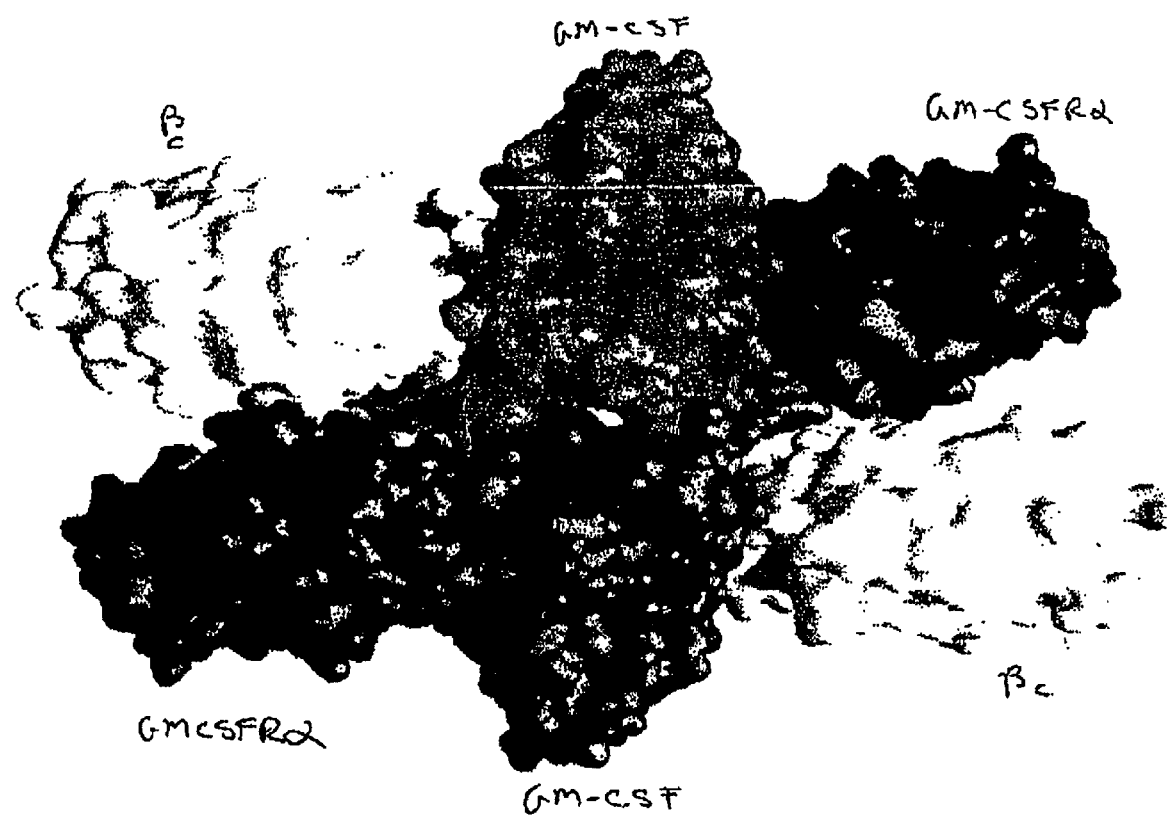

The modeling proceeded as follows: (i) A structure-based sequence alignment of the cytokine-binding homology regions (CHRs) from all known class 1 cytokine receptor structures was performed. The amino acid sequences of the GM-CSF α chain CHR and of domain 3 of β$_c$ were then added and manually aligned. The CHR of the α chain and domain 3 of β$_c$ were built by homology to the GHR crystal structure using the multiple sequence alignment as a guide. Loop regions were constructed from peptide fragment data bases and the models subjected to energy minimisation. The stereochemical quality of each model was judged excellent by the program PROCHECK [R. A. Laskowski, et al (1993)] and their correctness supported by 3D-1D scores that never fell below zero [R. Lüthy, et al (1992)]. (ii) The D4β$_c$ structure was superimposed on the corresponding domain of GHR. (iii) Domain 3 was connected to domain 4 based on the L-shaped orientation seen in the other class 1 cytokine receptors. The positioning was supported by the lack of steric overlap with BION-1 which also recognises a fragment of β$_c$ which includes domain's 3 and 4, the short 2 residue linker between the domains and the finding that the gp130 structure, which has no ligand bound, also has the domains in the same orientation. (iv) GM-CSF [K. Diederichs, et al (1991)] was docked onto its corresponding α chain manually using the GHR complex structure as a starting point and then optimising interactions using all the available mutagenesis data. (v) The cytokine-α chain complex was docked onto the modelled β chain by superimposing the GM-CSF component onto the hormone of the GHR complex (using a site 2 orientation in agreement with mutagenesis data. (vi) Small, rigid body adjustments were made manually on the cytokine-α chain complex, with respect to D4β$_c$ in order to optimise contact between cytokine and beta chain. (vi) The other cytokines, IL-3 [Y. Feng, et al (1996)] and IL-5 [M. V. Milburn et al., Nature 363, 172 (1993)], were superimposed onto GM-CSF of the modelled complex. (vii) The hexameric complex, consisting of 2 α subunits, 2 β subunits and 2 cytokine monomers, was constructed from the trimeric α subunit/β subunit/cytokine model by assuming a proper twofold exists between the two trimers. (Although deviations from a precise twofold relationship are quite possible, large deviations are not envisaged since all subunits have transmembrane regions that must stay imbedded in the membrane on complex formation). The modeling, together with biochemical data yielded two solutions in which the second trimer was located either clockwise or anticlockwise with respect to the first trimer when viewed down onto the membrane surface (FIG. 3). However, only one solution (FIG. 3) explained the importance of Tyr 421. Intriguingly, each monomer of the GM-CSF crystallographic dimer [Walter, M. R. et al (1992)] and of the IL-5 covalent dimer [M. V. Milburn et al (1993)] bind to each α chain in the preferred complex model.

Figure 2:
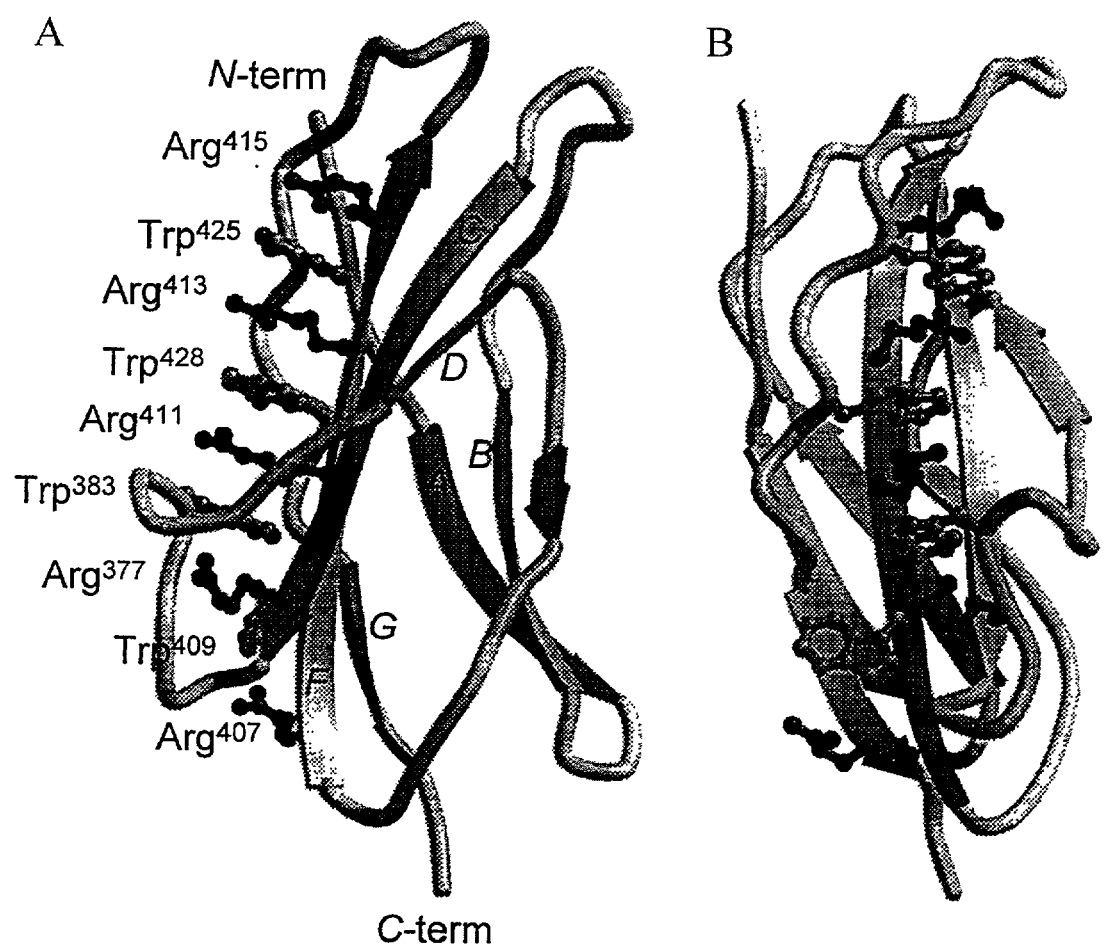
FIG. 2 illustrates a view of the Trp/Arg "ladder". The structure of the $D4\beta_c$ shown in ribbon representation with the side-chains of the Trp/Arg stack shown as ball-and-stick. The molecular graphics were produced using Molscript (Kraulis, 1991) and Raster3D (Merritt, and Murphy, 1994).

The resultant model reveals the following: (i) The membrane proximal domain of the α chain homology model possesses an elongated hydrophobic surface patch of dimensions 15 Å by 8 Å. Major contributors to the patch are Val 224, Val 226, Cys 228, Ile 313, Phe 315 and Gly 316 (GM-CSF α chain numbering). Most of these residues are conserved in α chains from different receptors and from different species (data not shown). (ii) The hydrophobic patch of the α chain is close enough to the H1 patch of D4$\beta_c$ to envisage an interaction between the two; however, the interaction area is likely small, consistent with data showing that there is little or no dimer formation observed in the absence of cytokine (Woodcock, J. M. et al (1997)). The corresponding H1 patch of GHR is also involved in subunit contacts (DeVos, A. M. et al (1992)). There are numerous interactions between each cytokine and the B'-C' loop. Significantly, the side-chains of Tyr 365, His 367, and Ile 368 form a cytokine-binding triad that converges closely at their tips to form a pivot point to which all three cytokines bind via the essential glutamate (Glu 21 of GM-CSF, Glu 22 of IL-3 and Glu 13 of IL-5) (Hercus, T. R. et al. (1994)). These observations are consistent with mutagenesis data that show Tyr 365, His 367 and Ile 368 are key GM-CSF binding determinants (Lock, P. et al. (1994)). Surprisingly, Tyr 421, the sole residue in the F'-G' loop implicated in high affinity binding (Woodcock, J. M. et al (1996)) is orientated away from the cytokine-binding site in the crystal structure (FIG. 1A). Biochemical data also shows that, whilst a Tyr 421 Phe mutation has a significant effect on the phosphorylation of the cytoplasmic domain, mutations in the B'-C' loop have a nominal effect (FIG. 2). An explanation for the critical role of this residue comes from the crystal structure and observations that the α,β heterodimer exists as a higher order complex (Lia, F. et al. (1996), Stomski, F. C. et al (1998)). A heterohexameric complex of two α chains, two β chains and two cytokines has been proposed based on the location of disulfide bridges in the GM-CSF receptor complex (Stomski, F. C. et al. (1998)) and by analogy to the IL-6 receptor system which has been shown to form a similar hexameric complex (Ward, L. D. et al. (1994)). We have modelled the hexameric complex and find that Tyr 421 is in an ideal position to interact with the second α chain of the complex (FIG. 3).

Figure 4:
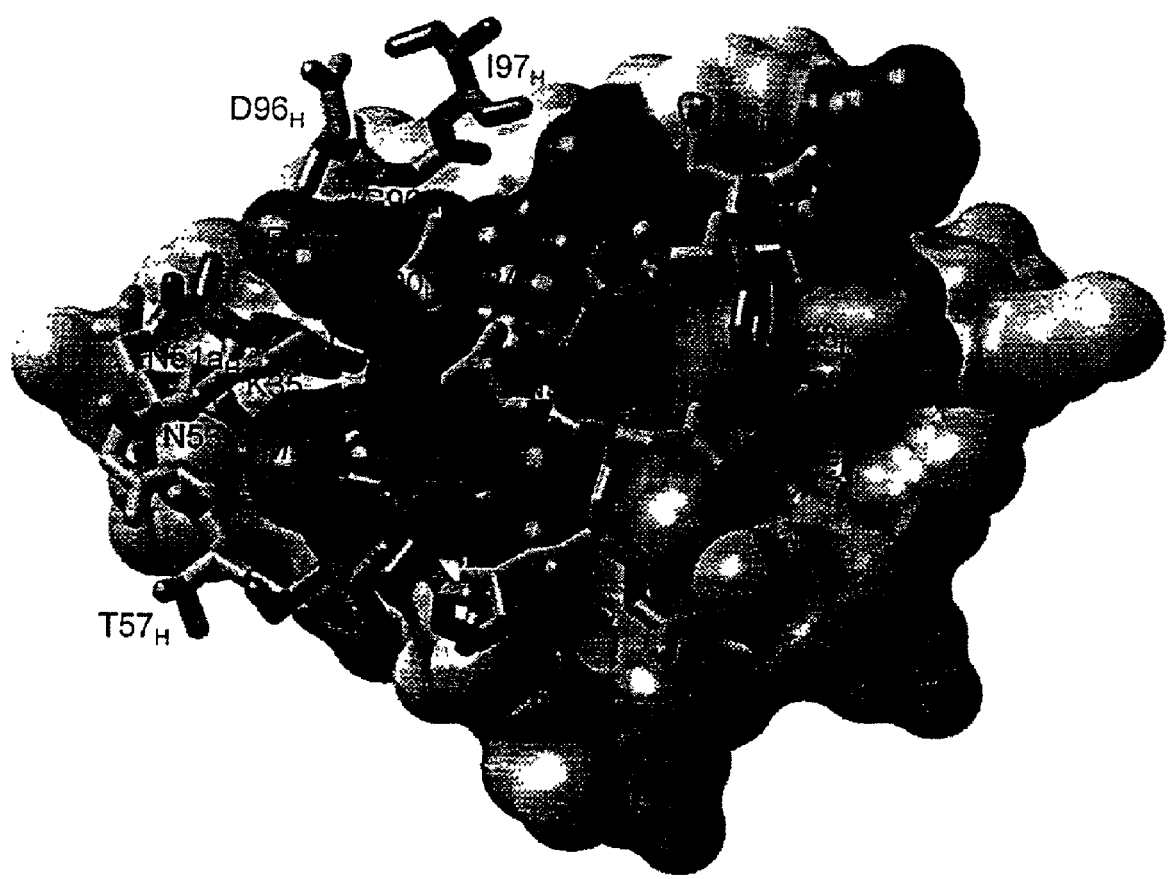
FIG. 4 illustrates the interactions and interface between the antibody (BION-1) and $D4\beta_c$.
Figure 5A:
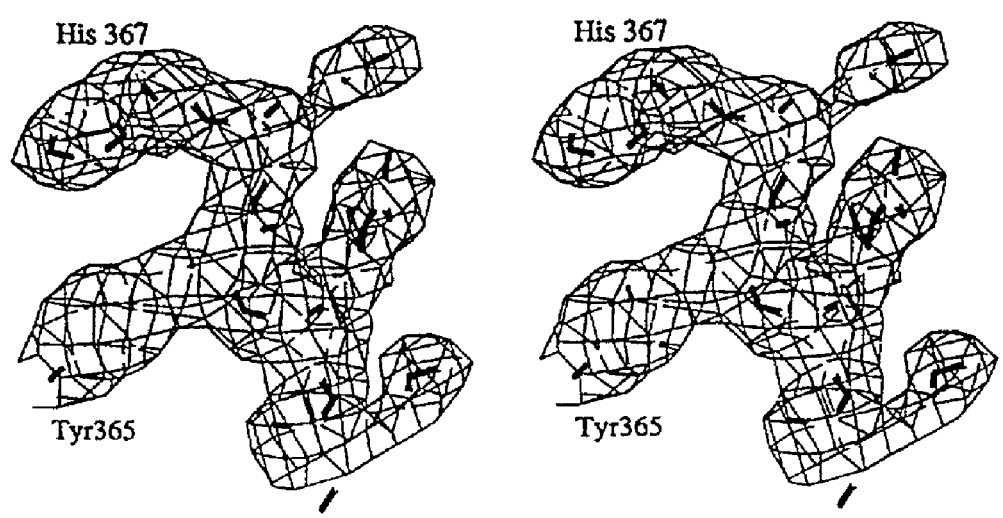
FIG. 5 illustrates a stereoview $2F_{obs}-F_{calc}$ electron density maps showing key regions of the receptor. The maps were calculated from the final model and contoured at 1c. (A) The B'-C' loop. (B) The extended WSXWS box.
Figure 5B:
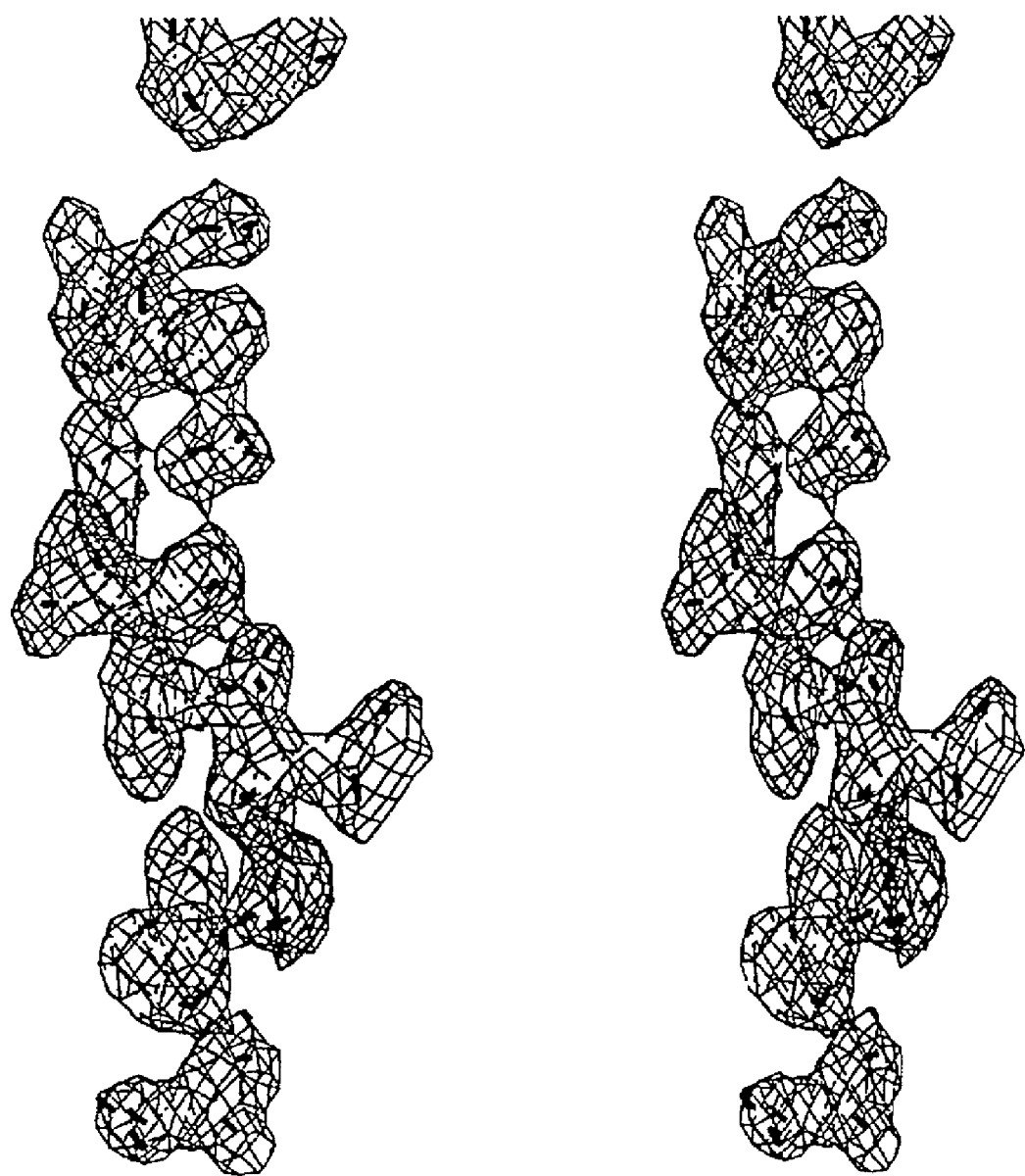

The monoclonal antibody antagonist, BION-1, forms extensive and intimate interactions with the receptor domain (FIG. 4 and Table 2). The total surface area buried on complex formation is 1,500 Å², which is in the range reported for other antibody-protein antigen complexes (Davies, D. R. and Cohen G. H. (1996)). In total, there are 2 salt bridges, 8 hydrogen-bonding Interactions and 86 van der Waals (vdw) interactions.

The contact surface comprises 15 residues from BION-1 with 9 residues from $V_H$ and 6 residues from $V_L$. The majority of contacts are roughly shared between four of the CDRs: CDR L1 (1 hydrogen bonds and 24 vdw contacts); CDR L3 (1 salt bridge, 3 hydrogen bonds and 20 vdw contacts); CDR H1 (1 salt bridge, 3 hydrogen bonds and 18 vdw contacts); CDR H3 (1 hydrogen bonds and 15 vdw contacts). In addition, CDR H2 provides a number of contacts (9 vdw contacts) but CDR L2 makes no contacts with the receptor domain. Modeling suggests that CDR L2 interacts with domain 3 of the intact b chain. In total, 6 residues from the B'-C' loop (between residues 362 and 368) and 4 residues from the F'-G' loop (between residues 416 and 422) are involved in antibody interactions. The B'-C' loop interacts with CDRs H1, H2, H3, L1 and L3 whereas the F'-G' loop interacts only with CDRs H3 and L1. The specific polar interactions between the B'-C' loop and the antibody are as follows: Lys 362 forms a salt bridge to Asp 94L, Glu 366 forms a salt bridge to Lys 35H, and the following residues form potential hydrogen bonding interactions: Arg 364 and Tyr 33H, Arg 364 (main-chain) and Tyr 33H, Tyr 365 and Glu 93L (main-chain), Tyr 365 and Asp 94L, Glu 366 and Tyr 33H (main-chain), His 367 and Asn 91L (main-chain). There are two potential hydrogen-bonding interactions involving the F'-G': Thr 416 and Tyr 28L, Arg 418 and Gly 96aH (main-chain). There is one small cavity of 9.9 Å³ in the antibody-antigen interface. The cavity is lined by residues Tyr 365, His 367 and Ile 368 of the receptor and Val 27, Tyr 28, Phe 32 and Asn 92 of the antibody light chain.

The B'-C' loop of D4$\beta_c$ is nestled in the shallow antigen-binding groove between the $V_H$ and $V_L$ domains whereas the F'-G' loop forms a more peripheral interaction with CDR L1 of BION-1. Interactions from the B'-C' loop account for 75% of the total interactions of D4$\beta_c$ with BION-1. Of particular note are numerous aromatic interactions involving aromatic residues from BION-1 and Tyr 365 and His 367 of the receptor (FIG. 4 and Table 2). These types of interactions are a common feature at antibody combining sites.

The epitope of D4$\beta_c$ recognised by BION-1 largely overlaps the surface that interacts with the cytokines. Furthermore, BION-1 inhibited the GM-CSF/IL-3/IL-5-induced proliferation of eosinophils in vitro, highlighting the feasibility of single molecule antagonists of several cytokines. This multi-hit approach may prove useful in allergic inflammation and cancer where more than one cytokine is frequently associated with these diseases. The structure presented here provides a number of possibilities for the design of novel therapeutics: (i) The affinity of BION-1 for intact β chain is 50 nM in contrast to high affinity cytokine-binding of 0.1 nM. The structure provides the opportunity of engineering a higher affinity antibody or corresponding small molecule mimetic, such as a cyclized, mutated version of a major contributing CDR from BION-1. (ii) The presence of the groove at the cytokine-binding interface is an appealing site for the design of small molecule antagonists. (iii) The location of Tyr 421 at a critical subunit interface provides another distinct target for structure-based inhibitor design.

Example 3

Functional Roles of the B-C Loop and Tyr$^{421}$

Figure 6A:
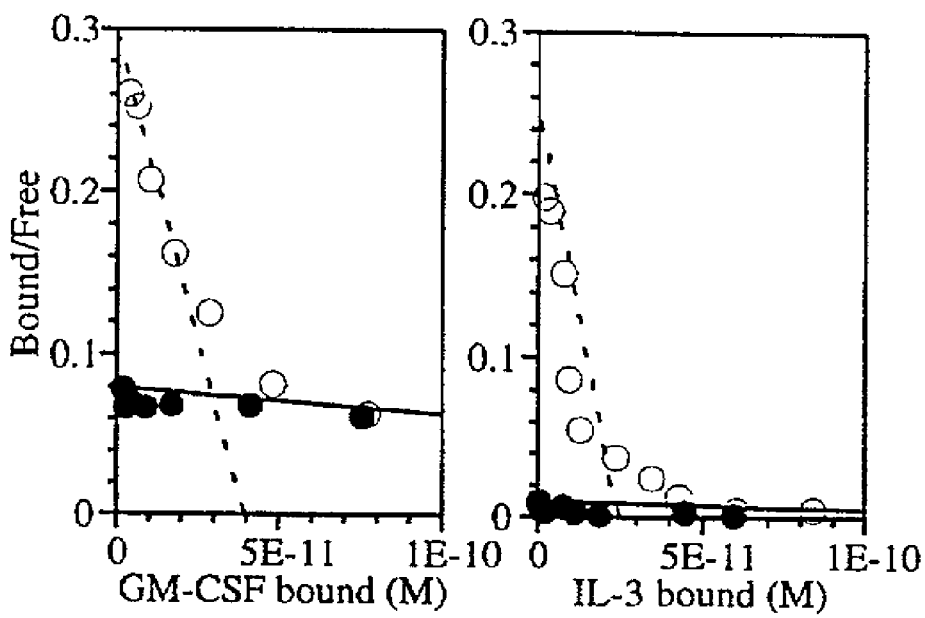
FIG. 6 illustrates the differential effects of mutating the B-C loop and/or $Tyr^{421}$ of the F-G loop in receptor activation. (A) Scatchard transformation of binding isotherms for $^{125}I$-GM-CSF and $^{125}I$-IL-3 binding to cells transfected with wild type $\beta_c$ (E) or $^{365}AAAA^{368}$ mutant $\beta_c$ ( ). (B) Western blot of wild type and mutant $\beta_c$ after stimulation with various concentrations of IL-3. The blot was probed for phosphotyrosine (upper panel) and $\beta_c$ (lower panel). The double bands in each lane of the gels represent glycosylation variants of $\beta_c$ (Woodcock, J. M. et al (1997) Blood 90: 3005).
Figure 6B:
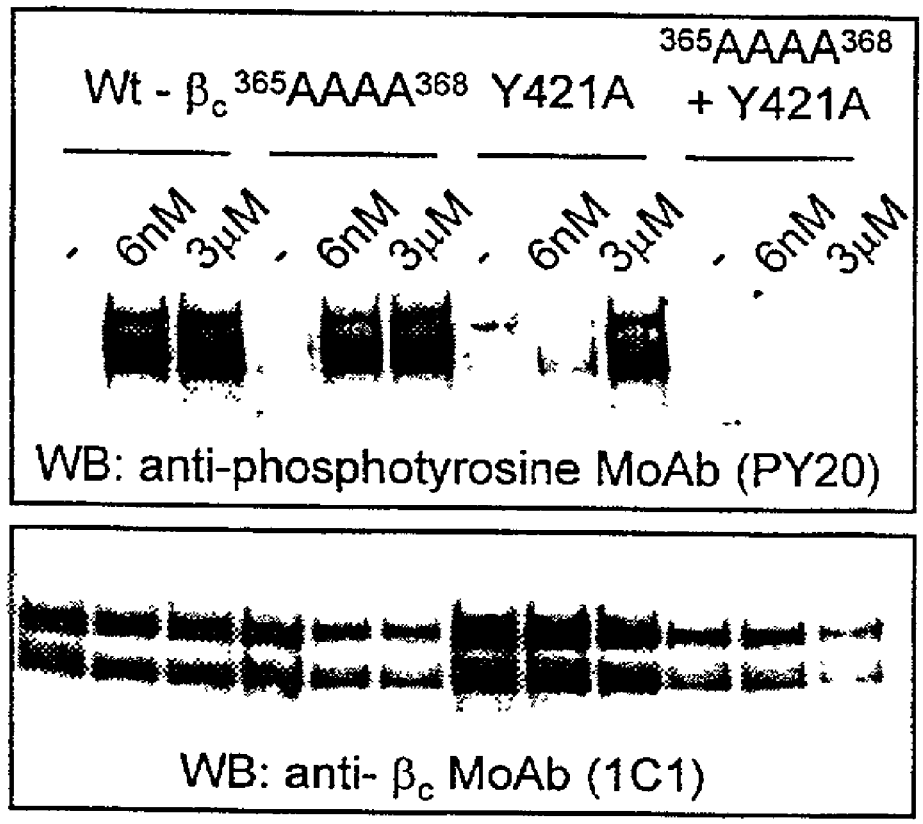
Figure 7:
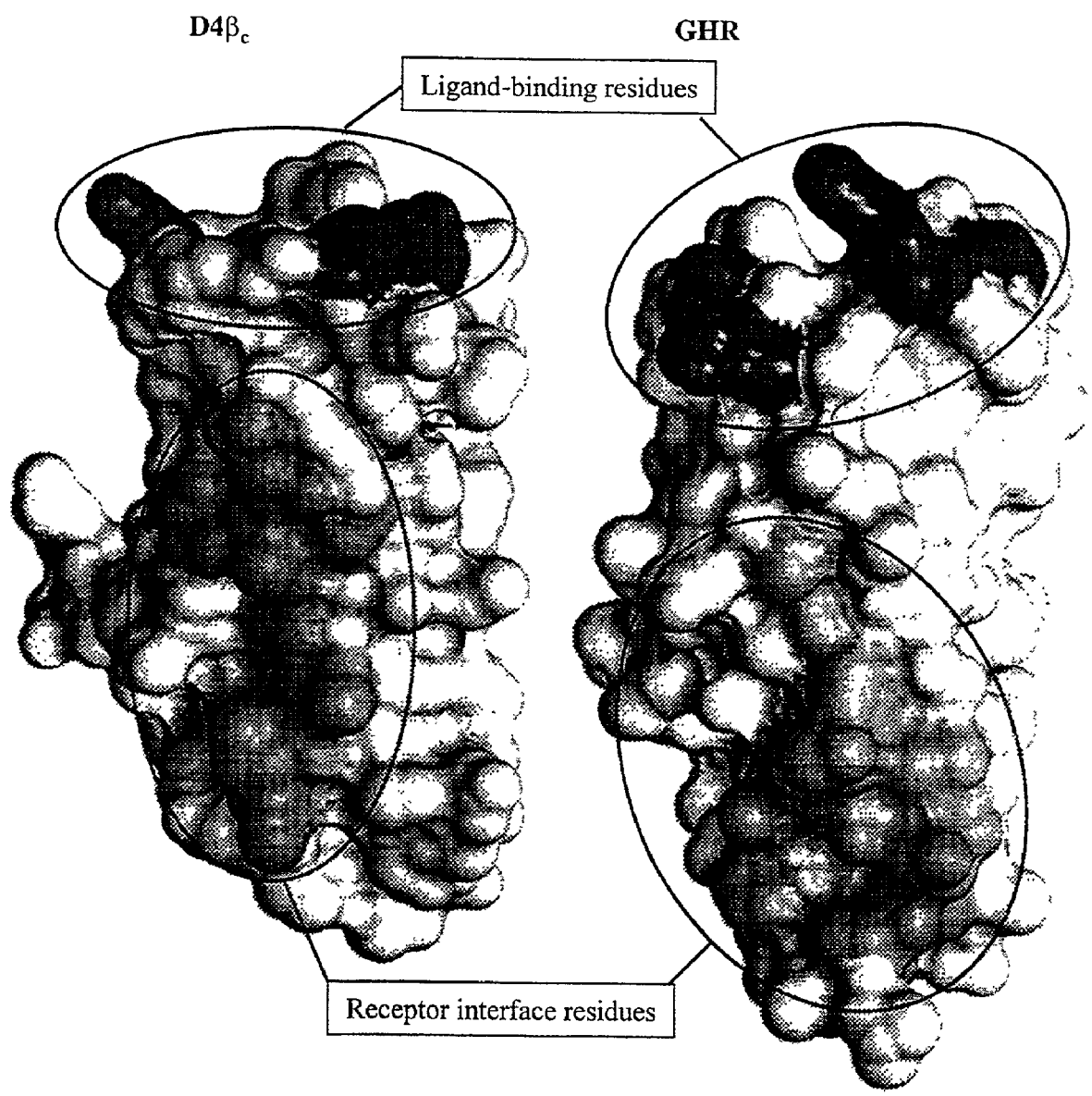
FIG. 7 illustrates a comparison of $D4\beta_c$ with the membrane-proximal domain of GHR. $D4\beta_c$ and domain two of the subunit of the GHR that interacts with the helix A/helix C face of GH were aligned structurally via their core residues and are shown as surface representations using the program InsightII (MSI). The hydrophobic/aromatic patch, H2, of $D4\beta_c$ and the location of the site of GHR that interacts with the opposing receptor molecule are indicated by darkened surfaces and are ringed and labelled "Receptor interface residues". The dark surfaces of $D4\beta_c$ indicating the region known to interact with GH are ringed and labelled "Ligand-binding residues".

Although the structure of D4$\beta_c$ revealed that Tyr$^{421}$ is in close proximity to the three residues in the B-C loop involved in cytokine binding (Tyr$^{365}$, His$^{367}$ & Ile$^{368}$) the side-chain is oriented away from these possibility reflecting different functional roles. Previous experiments suggested that high-affinity binding of IL-3 was sensitive to mutation of Tyr$^{421}$ (Woodcock, J. M. (1996)) but not to replacement of individual residues in the B-C loop (Woodcock, J. M. et al (1994)). We examined whether a multiple mutation in the B-C loop of the residues implicated in binding GM-CSF and IL-5 would affect IL-3 high-affinity binding. The results showed (FIG. 6A) that alanine substitution of residues 365 to 368 in the B-C loop abrogated high-affinity binding of both GM-CSF and IL-3. We next examined phosphorylation of cytoplasmic tyrosine residues as this is a very sensitive measure of recruitment of $\beta_c$ to a ligand/$\alpha$-chain complex. Analogs of $\beta_c$ that are unable to affinity-convert due to the affinity of the $\alpha$/$\beta$ complex for cytokine being less than or equal to that of $\alpha$-chain alone may nevertheless exhibit differences in tyrosine phosphorylation. We examined the effects of mutating the B-C loop or Tyr$^{421}$, either separately or in combination, on the ability of $\beta_c$ to undergo tyrosine phosphorylation in response to IL-3. We found that substitution of Tyr$^{421}$ had a pronounced effect with high levels of tyrosine phosphorylation of $\beta_c$ being achieved only at 3 μM IL-3, a concentration about 500-fold higher than required by the native receptor (6 nM). In contrast, mutation of the B-C loop alone did not impair IL-3-induced phosphorylation of $\beta_c$ at the high concentration used. Nevertheless, a role for the B-C loop in $\beta_c$ activation was demonstrated by a combined mutant of the B-C loop and Tyr$^{421}$ (FIG. 6B) which abrogated IL-3-induced tyrosine phosphorylation of $\beta_c$.

Example 4

Antagonist Interactions with the $\beta_c$ Activation Domain

A detailed analysis of the structure of the BION-1/D4$\beta_c$ complex confirmed and extended these observations with BION-1 seen to form extensive and intimate interactions with the receptor activation domain (FIGS. 1A,B and 7). The total surface area buried on complex formation is 1,500 Å$^2$, which is in the range reported for other antibody-protein antigen complexes(Davies, D. R. and Cohen, G. H. (1996)). In total, there are 2 salt bridges (Lys$^{362}$/Asp$^{L94}$ and Glu$^{366}$/Lys$^{H35}$), 8 potential hydrogen-bonds and 124 van der Waals (vdw) interactions (Table 2). The B-C loop of D$^{4\beta}_c$ is nestled in the shallow antigen-binding groove between the V$_H$ and V$_L$ domains whereas the F-G loop forms a more peripheral interaction with CDR L1 of BION-1 (FIGS. 1A,B and 7). The contact surface comprises 14 residues from BION-1 with 9 residues from V$_H$ and 5 residues from V$_L$. The majority of contacts are roughly shared between four of the CDRs: CDR L1 (1 hydrogen bond and 29 vdw contacts); CDR L3 (1 salt bridge, 3 hydrogen bonds and 28 vdw contacts); CDR H1 (1 salt bridge, 3 hydrogen bonds and 36 vdw contacts); CDR H3 (1 hydrogen bond and 23 vdw contacts). In addition, CDR H2 provides a number of contacts (8 vdw contacts) but CDR L2 makes no contacts with the receptor domain. In total, 6 residues from the B-C loop (between residues 362 and 368) and 3 residues from the F-G loop (between residues 416 and 422) of D$^{4\beta}_c$ are involved in antibody interactions with those from the B-C loop accounting for 75% of the total. The B-C loop interacts with CDRs H1, H2, H3, L1 and L3 whereas the F-G loop interacts only with CDRs H3 and L1 (FIG. 4). There is one small cavity of 9.9 Å$^3$ in the antibody-antigen interface. The cavity is lined by residues Tyr$^{365}$, His$^{367}$ and Ile$^{368}$ of the receptor and Val$^{27}$, Tyr$^{28}$, Phe$^{32}$ and Asn$^{92}$ of the antibody light chain. Not all of the potential salt bridges and hydrogen bonds identified above are likely to contribute productively to complex formation since substitution analysis has only identified Glu$^{366}$, Arg$^{418}$ and Met$^{363}$ or Arg$^{364}$ in D4$\beta_c$ as contributing to the epitope for binding BION-1 (Sun, Q. et al (1999) Blood, 1943) (Table 2).

Finally it is to be understood that various other modifications and/or alterations may be made without departing from the spirit of the present invention as outlined herein.

REFERENCES

1. P. Lock, D. Metcalf, N. A. Nicola, *Proc. Natl. Acad. Sci. USA* 91, 252 (1994);
2. J. M. Woodcock et al., *EMBO J.* 13, 5176 (1994).
3. J. M. Woodcock, C. J. Bagley, B. Zacharakis, A. F. Lopez, *J. Biol. Chem.* 271, 25999 (1996).
4. A. M. De Vos, M. Ultsch, A. A. Kossiakoff, *Science* 255, 306 (1992).
5. J. M. Woodcock et al., *Blood* 90, 3005 (1997).
6. T. R. Hercus et al., *Blood* 83, 3500 (1994); S. C. Barry et al., *J. Biol. Chem.* 269, 8488 (1994); J. Tavernier et al., *Proc. Natl. Acad. Sci. USA* 92, 5194 (1995).
7. F. Lia, D. Rajotte, S. C. Clark, T. Hoang, *J. Biol. Chem.* 271, 28287 (1996); F. C. Stomski et al., *Mol. Cell. Biol.* 16, 3035 (1996); B. J. Jenkins, T. J. Blake, T. J. Gonda, *Blood* 92, 1989 (1998).
8. F. C. Stomski et al., *J. Biol. Chem.* 273, 1192 (1998).
9. L. D. Ward et al., *J. Biol. Chem.* 269 23286 (1994).
10. D. R. Davies and G. H. Cohen, *Proc. Natl. Acad. Sci. USA* 93, 7 (1996).
11. A. F. Lopez et al (1989) Proc. Natl. Acad. Sci. USA. 86, 7022-7026.
12. A. F. Lopez et al (1990) J. Cell Physiol. 145, 69-77.
13. Z. Otwinowski and W. Minor, *Methods Enzymol.* 276, 207 (1997).
14. J. Navaza, *Acta Crystallogr. A* 50, 157(1994).
15. J. B. Charbonnier, et al *Science* 275, 1140 (1997).
16. T. A. Jones, J.-Y. Zou, S. W. Cowan, M. Kjeldgaard, *Acta Crystallogr. A* 47, 110 (1991).
17. A. T. Brunger et al., *Act Crystallogr. D.* 54, 905 (1998).
18. R. Lüthy, J. U. Bowie, D. Eisenberg, *Nature* 356, 83 (1992).
19. R. A. Laskowski, M. W. MacArthur, D. S. Moss, J. M. Thornton, *J. Application. Crystallogr.* 26, 283 (1993).
20. R. A. Laskowski, M. W. MacArthur, D. S. Moss, J. M. Thornton, *J. Application. Crystallogr.* 26, (1993).
21. K. Diederichs, T. Boone, P. A. Karplus. *Science* 254, 1779 (1991).
22. Y. Feng, B. K. Klein, C. A. McWherter, *J. Mol. Biol.* 259, 524 (1996).
23. Walter M. R. et al (1992).
24. T. Walter M. R. Cook W. J. Ealick S. E., Nagabhushan T. L., Trotta P. O. and Bugg C. E. *J. Mol. Bio.* 224,1075-1085, (1992).
25. M. Wills-Karp, J. Luyimbazi, X. Xueying, B. Schofield, T. Y. Neben, C. L. Karp, D. D. Donaldson, *Science* 282, 2258 (1998).
26. G. Grunig, M. Warnock, A. E. Wakil, R. Venkayya, F. Brombacher, D. M. Rennick, D. Shepard, M. Mohrs, D. D. Donaldson, R. M. Locksley, D. B. Corry, *Science,* 282, 2261 (1998).

What is claimed:

1. A cytokine-binding domain of an isolated Domain 4 of a $\beta_c$ chain (D4$\beta_c$) of a human cytokine receptor selected from the group consisting of GM-CSF receptor, IL-3 receptor, and IL-5 receptor, and consisting of a portion of amino acid residues 338-438 of D4$\beta_c$, the portion capable of binding to at least one cytokine and transducing a cytokine signal through a single cytokine receptor, said cytokine-binding domain comprising a B'-C' loop of D4$\beta_c$ comprising residues Lys362, Met363, Arg364, Tyr365, Glu366, and His367, a F'-G' loop comprising residues Thr416, Arg418, and Tyr421, and a groove located at an N-terminal end of the cytokine-binding domain where one wall of the groove is formed by the B'-C' loop and the F'-G' loop and the other wall of the groove is formed by residues 338-342 of D4$\beta_c$.

2. The cytokine-binding domain according to claim 1 wherein the F'-G' loop comprises Arg418 and Tyr421 of D4$\beta_c$ and the N-terminal end of D4$\beta_c$.

3. The cytokine-binding domain according to claim 1 comprising Tyr421 of D4$\beta_c$.

4. The cytokine-binding domain according to claim 1 wherein the B'-C' loop residues of D4$\beta_c$ form a type 1 β-turn.

5. The cytokine-binding domain according to claim 1, wherein the cytokine-binding domain is defined by an area bordered by any one of the following residues selected from the group consisting of Lys362, Met363, Arg364, Tyr365, Glu366, His367, Thr416, Arg418, and Tyr421.

6. The cytokine-binding domain according to claim 1 that binds to at least two cytokines selected from the group consisting of IL-3, IL-5 and GM-CSF.

7. The cytokine-binding domain according to claim 2 wherein the F'-G' loop adopts a type IV β-turn.

8. The cytokine-binding domain according to claim 1 which comprises a hydrophobic patch, said patch comprising residues Ile338, Ala341, Met361, and Tyr365 of D4$\beta_c$ and which forms a lip at an end of a groove on the surface of the cytokine-binding domain.

9. The cytokine-binding domain according to claim 8 further comprising Met340, Pro342, and Lys362 of D4$\beta_c$.

10. The cytokine-binding domain according to claim 8 further comprising Ile368 or Tyr421of D4$\beta_c$.

11. The cytokine-binding domain according to claim 1 wherein the B'-C' loop comprises residues 362 to 368 of D4$\beta_c$.

12. The cytokine-binding domain according to claim 1 wherein the F'-G' loop comprises residues 416 to 422 of D4$\beta_c$.

13. The cytokine-binding domain according to claim 1 wherein the B'-C' loop comprises residues Tyr365, His367, Ile368 of D4$\beta_c$ which form a cytokine-binding triad that converges to form a pivot point.

14. The cytokine-binding domain according to claim 1 wherein a type 1 β-turn is formed from residues 365 to 368 of D4$\beta_c$.

15. The cytokine-binding domain according to claim 7 wherein the type IV β-turn comprises Arg418 and Tyr421 which Tyr421 projects away from the structure.

16. The cytokine-binding domain according to claim 1 wherein the B'-C' loop consists of residues Lys362, Met363, Arg364, Tyr365, Glu366, and His367.

17. The cytokine-binding domain according to claim 1 wherein the F'-G' loop consists of residues Thr416, Arg418, and Tyr421.

18. The cytokine-binding domain according to claim 1 consisting of amino acid residues 338-421 of $D4\beta_c$.

* * * * *